(12) United States Patent
Iwamatsu

(10) Patent No.: US 10,036,693 B2
(45) Date of Patent: Jul. 31, 2018

(54) METHOD AND APPARATUS FOR EVALUATING DUCTILE FRACTURE

(71) Applicant: Hitachi, Ltd., Chiyoda-ku, Tokyo (JP)

(72) Inventor: Fuminori Iwamatsu, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 26 days.

(21) Appl. No.: 15/110,324

(22) PCT Filed: Feb. 17, 2014

(86) PCT No.: PCT/JP2014/053577
§ 371 (c)(1),
(2) Date: Jul. 7, 2016

(87) PCT Pub. No.: WO2015/122000
PCT Pub. Date: Aug. 20, 2015

(65) Prior Publication Data
US 2016/0327463 A1 Nov. 10, 2016

(51) Int. Cl.
| | | |
|---|---|---|
| G01B 3/52 | (2006.01) | |
| G01N 3/28 | (2006.01) | |
| G01N 3/08 | (2006.01) | |
| G01N 3/12 | (2006.01) | |
| G01M 5/00 | (2006.01) | |
| G01N 3/20 | (2006.01) | |

(52) U.S. Cl.
CPC ............ G01N 3/28 (2013.01); G01M 5/0033 (2013.01); G01N 3/08 (2013.01); G01N 3/12 (2013.01); G01N 3/20 (2013.01); *G01N 2203/0062* (2013.01)

(58) Field of Classification Search
CPC .. G01N 3/28; G01N 3/20; G01N 3/08; G01N 3/12; G01N 2203/0062; G01M 5/0033

USPC ............... 73/849, 851, 799; 702/34, 42, 35
See application file for complete search history.

(56) References Cited

FOREIGN PATENT DOCUMENTS

| | | |
|---|---|---|
| JP | 8-122221 A | 5/1996 |
| JP | 2011-27493 A | 2/2011 |
| JP | 2012-247271 A | 12/2012 |

OTHER PUBLICATIONS

Iwamatsu et al. "Estimation of Maximum Load for Pipes with Multiple Circumferential Flaws by Limit Load Analysis" Proceedings of the ASME 2011 Pressure Vessels & Piping Division Conference, PVP2011, Jul. 17-21, 2011. <http://citeseerx.ist.psu.edu/viewdoc/download?doi=10.1.1.660.6139&rep=rep1&type=pdf>.*
International Search Report (PCT/ISA/210) issued in PCT Application No. PCT/JP2014/053577 dated Apr. 15, 2014 with English-language translation (four (4) pages).

* cited by examiner

Primary Examiner — Jonathan Dunlap
(74) Attorney, Agent, or Firm — Crowell & Moring LLP

(57) ABSTRACT

An object of the invention is to provide a simple method and apparatus for evaluating a collapse load of a structure with respect to ductile fracture in the case where a plurality of flaws exist in a cylindrical structure that receives a bending load. The invention is an evaluation method and apparatus in which a result obtained by calculating a collapse load while a flaw having the largest area among a plurality of flaws is considered as a single flaw and a result obtained by replacing a plurality of flaws with penetration flaws corresponding to the plurality of flaws and calculating a collapse load are compared with each other and the smallest collapse load is set to be a collapse load of a structure.

1 Claim, 10 Drawing Sheets

[FIG. 6]
| No. | $\theta_1$, deg. | $\theta_2$, deg. | $a_1/t$ | $a_2/t$ |
|---|---|---|---|---|
| 1 | 20 | 20 | 0.75 | 0.75 |
| 2 | 20 | 40 | 0.75 | 0.75 |
| 3 | 20 | 60 | 0.75 | 0.75 |
| 4 | 60 | 20 | 0.75 | 0.75 |
| 5 | 60 | 40 | 0.75 | 0.75 |
| 6 | 60 | 60 | 0.75 | 0.75 |
[FIG. 7]
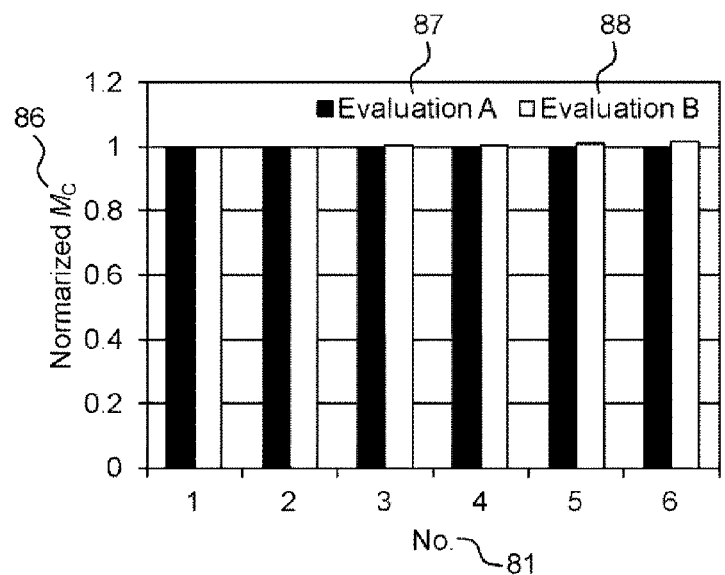

[FIG. 10]
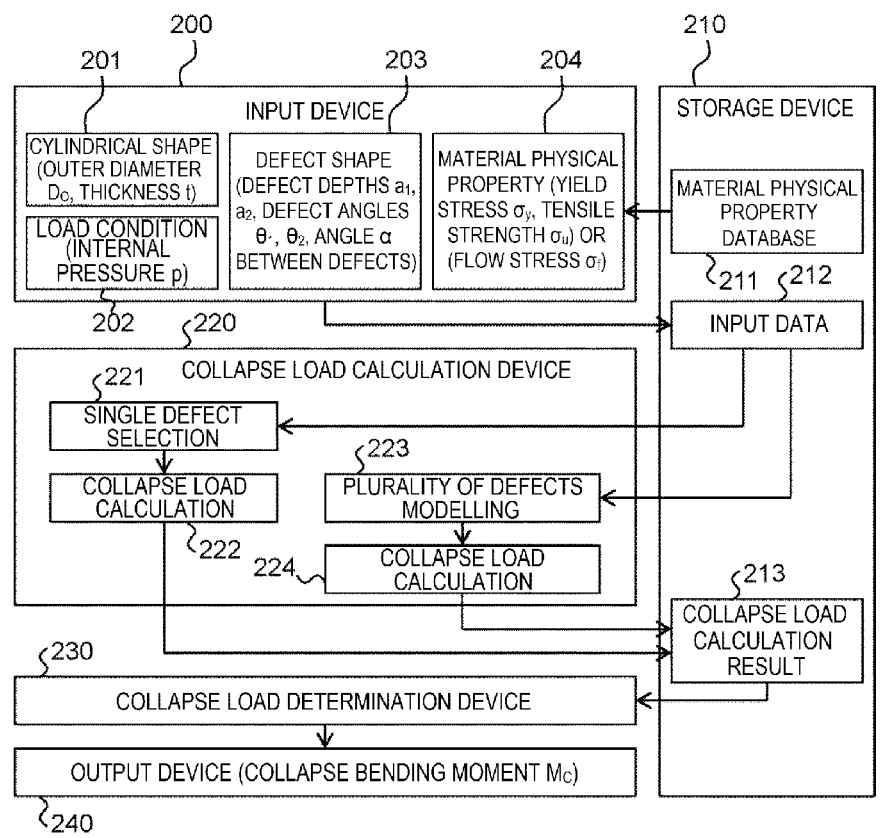

[FIG. 11]
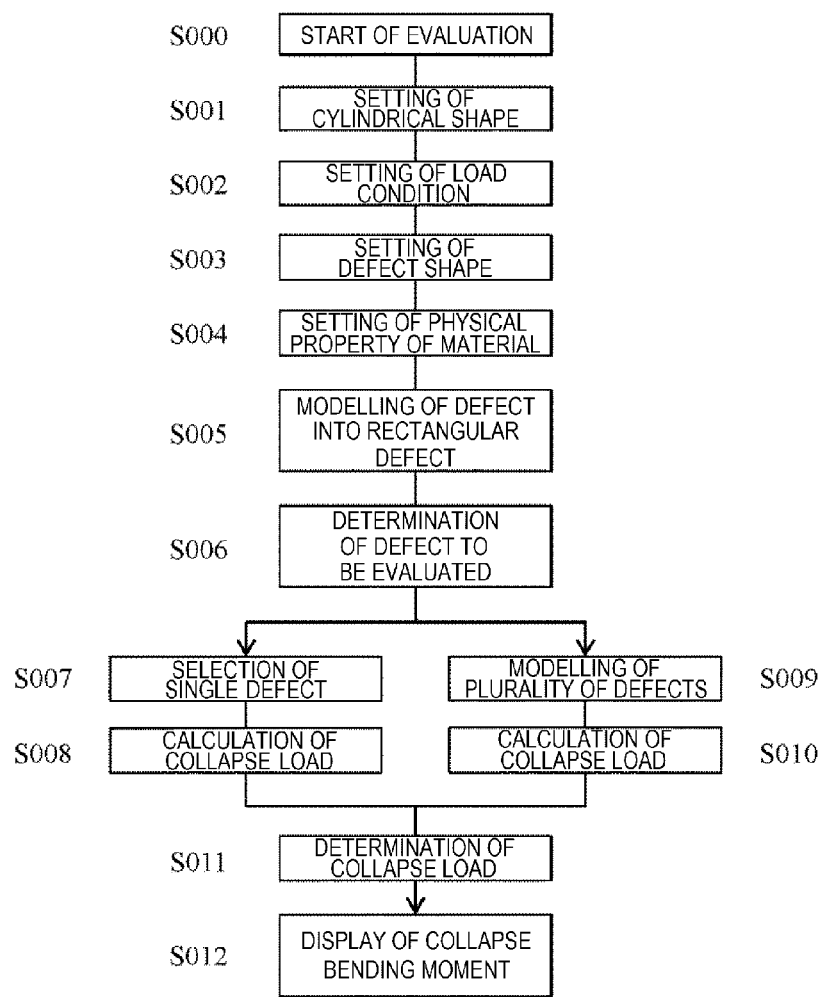

METHOD AND APPARATUS FOR EVALUATING DUCTILE FRACTURE

TECHNICAL FIELD

The present invention relates to a method and apparatus for evaluating a collapse load in a cylindrical structure in which ductile fracture is assumed as a damage mode when the cylindrical structure receives an excessive bending load.

BACKGROUND ART

Welding is widely used to bond structures such as pipes in a power plant, a chemical plant, and the like. In some cases, a residual stress is generated in the vicinity of a welded portion that has subjected to welding. When the welded portion is exposed to high temperature water or the like for a long time while a tensile residual stress remains in the welded portion, stress corrosion cracking occurs and therefore a plurality of crack-like flaws are generated on the same plane or at adjacent positions. Ductile fracture or brittle fracture may occur in the structure having the plurality of flaws. In view of this, in order to prevent the above fracture, a fracture load of the structure having the plurality of flaws is calculated. As a method for calculating such a fracture load, for example, a technology disclosed in PTL 1 is known.

PTL 1 discloses that a fracture evaluation apparatus for a pipe includes a setting unit for setting any transverse section to be evaluated, a setting unit for setting a region of a crack existing in the transverse section, a setting unit for setting a neutral axis with respect to a bending moment acting on a pipe, a changing unit for changing a direction of the neutral axis, a calculation unit for calculating a fracture mechanics parameter along a front edge of a crack in the case where the bending moment corresponding to the neutral axis acts, a detection unit for detecting a local maximum of a distribution curve of the fracture mechanics parameter, a selection unit for selecting an evaluation neutral axis in which the local maximum can be a global maximum, and an evaluation unit for evaluating fracture caused by an action of the bending moment corresponding to the evaluation neutral axis, and therefore, in the case where integrity of a pipe is evaluated, excessive maintainability is removed and a realistic and reasonable fracture evaluation technology for a pipe is provided.

CITATION LIST

Patent Literature

PTL 1: JP-A-2011-27493

SUMMARY OF INVENTION

Technical Problem

Depending on a material or a portion of a structure such as a welded portion, a plurality of flaws are generated in some cases. In the case where a plurality of flaws exist in a cylindrical structure that receives a bending load, collapse load values leading to fracture are different depending on a direction of the bending load. Therefore, in PTL 1, in fracture evaluation of a pipe in which a plurality of flaws exist, a neutral axis is set with respect to a bending moment, and a direction of this neutral axis is changed, and then a fracture mechanics parameter is calculated for each changed neutral axis. In the technology disclosed in PTL 1, in order to obtain an appropriate result of fracture evaluation, repeat calculation needs to be performed with respect to the most critical flaw about 10 or more but 100 or less times. Note that, the greater the number of flaws existing in a structure is, the greater an influence of a positional relationship between the flaws on a collapse load at the time of fracturing is, and therefore it is difficult to determine a critical flaw.

The invention has been made in view of such problems, and an object thereof is to provide a simple method and apparatus for evaluating a collapse load of a structure with respect to ductile fracture in the case where a plurality of flaws exist in a cylindrical structure that receives a bending load.

Solution to Problem

The inventors of the invention had been diligently studied to solve the above problems, and, as a result, the inventors found that the above problems can be solved as follows: a result obtained by calculating a collapse load while a flaw having the largest area among a plurality of flaws is considered as a single flaw and a result obtained by replacing a plurality of flaws with penetration flaws corresponding to the plurality of flaws and calculating a collapse load are compared with each other; and the smallest collapse load is set to be a collapse load of a structure.

Advantageous Effects of Invention

According to the invention, it is possible to provide a method and apparatus for evaluating a collapse load with respect to ductile fracture in the case where a plurality of flaws exist in a cylindrical structure that receives a bending load.

BRIEF DESCRIPTION OF DRAWINGS

FIG. 6 is a table showing evaluation conditions of the example of a cylinder having flaws in FIG. 5.

FIG. 7 is a graph showing evaluation results of the example of the cylinder having the flaws in FIG. 5.

FIG. 10 shows an apparatus that can implement the method for evaluating ductile fracture according to this embodiment.

FIG. 11 shows a processing flow of the method for evaluating ductile fracture according to this embodiment.

DESCRIPTION OF EMBODIMENTS

Hereinafter, an embodiment of the invention (this embodiment) will be described.

[1. Introduction]

A method for evaluating ductile fracture according to this embodiment (an evaluation method according to this embodiment) is to calculate a collapse load with which, upon receipt of a bending load, a cylindrical structure such as a pipe in which a plurality of flaws exist is collapsed due to ductile fracture. That is, when a load exceeding a collapse load is applied to a structure having a plurality of flaws, ductile cracks are extended from the flaws, which results in collapse of the structure. Further, the evaluation method according to this embodiment is applied to evaluation of a cylindrical structure in which ductile fracture is assumed when the cylindrical structure receives a bending load. It is important to easily calculate a collapse load in order to easily prevent fracture of a structure.

Conventionally, a collapse load of ductile fracture has been analytically calculated by using various parameters such as a material of a structure, a depth and a width of a flaw existing in the structure, and a distance between flaws. This calculation is applicable only in the case where a single flaw exists. In the case where a plurality of flaws exist, a collapse load is calculated assuming that the plurality of flaws are integrated and exist as a single flaw. Therefore, when the number of or size of flaws is different, calculation of a collapse load is complicated or accuracy is reduced in some cases.

In view of this, the inventors of the invention found that, when a plurality of flaws exist in a cylindrical structure such as a pipe, a collapse load of ductile fracture of the structure caused by a bending load is calculated by using an evaluation method in which such flaws are replaced with corresponding flaws, and therefore the collapse load can be easily and accurately calculated.

Hereinafter, a method for evaluating ductile fracture according to this embodiment will be described. After that, a method for selecting a target flaw and a method for determining a corresponding penetration flaw in the method for evaluating ductile fracture will be described in [3. Method for determining flaw to be evaluated in method for evaluating ductile fracture according to this embodiment] and [4. Method for determining corresponding penetration flaw in method for evaluating ductile fracture according to this embodiment] described below.

[2. Method for Evaluating Ductile Fracture According to this Embodiment]

Figure 1A:
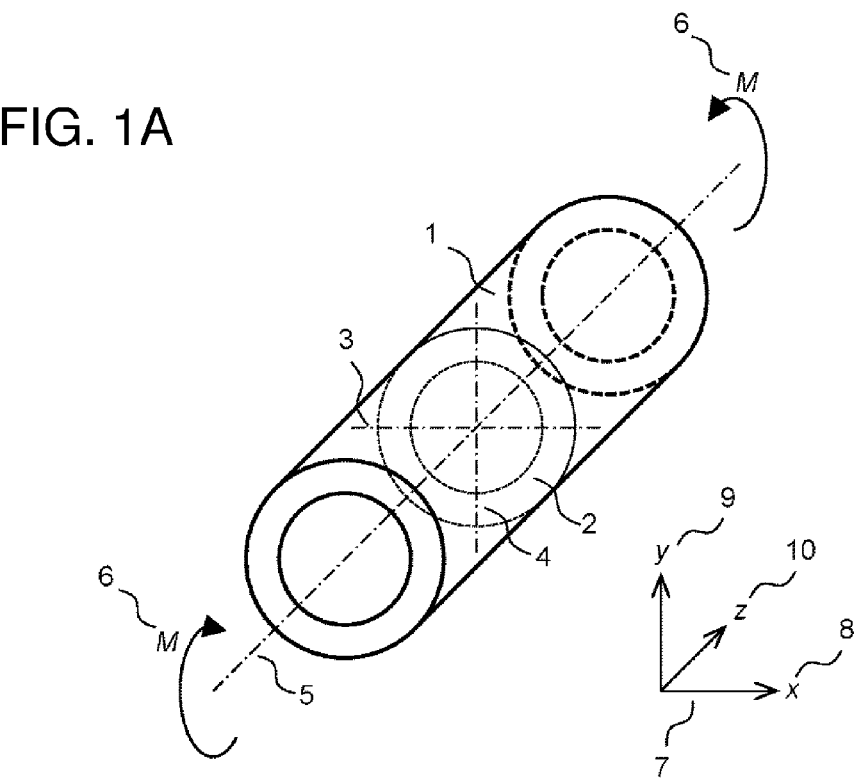
FIGS. 1A and 1B illustrate a cylinder having flaws to which a method for evaluating ductile fracture according to this embodiment is applicable.
Figure 1B:
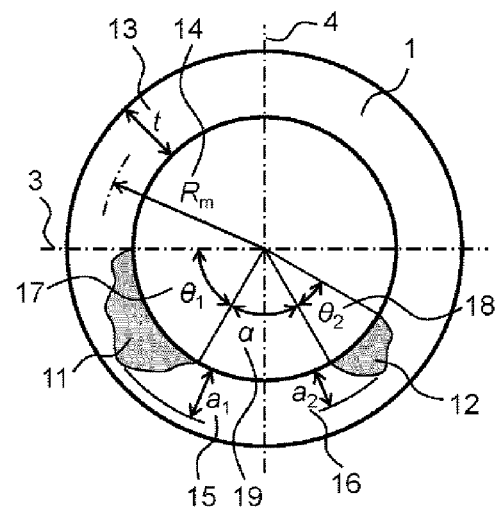

FIG. 1 illustrates a cylinder having flaws to which a method for evaluating ductile fracture according to this embodiment is applicable. FIG. 1(a) illustrates a general view, and FIG. 1 (b) illustrates a cross-sectional view in which flaws exist.

A cylinder 1 illustrated in FIG. 1(a) has crack-like flaws 11 and 12 in a cross-section 2 vertical to an axial direction 5 of a center axis of the cylinder 1. Note that, in a rectangular coordinate system 7 indicated by an x-direction 8, a y-direction 9, and a z-direction 10, the z-direction 10 is defined to correspond to the axial direction 5. The cylinder 1 receives a bending moment 6 in which an axis vertical to the z-direction 10, e.g., the x-direction 8 serves as a rotation axis. As to the flaws 11 and 12 existing in the cross-section 2, flaw depths $a_1$ 15 and $a_2$ 16, flaw lengths or angles $\theta_1$ 17 and $\theta_2$ 18, and a distance or angle $\alpha$ 19 between the flaws 11 and 12 are measured by an inspection method such as ultrasonic testing. Note that, in fracture evaluation performed in the case where the cylinder 1 receives the bending moment 6, when the flaws 11 and 12 and the cross-section 2 have angles, dimensions projected on the cross-section 2 are measured. Values of a thickness 13 and an average radius $R_m$ 14 in the cross-section 2 of the cylinder 1 are also obtained by, for example, using a design drawing or performing measurement.

FIG. 2 illustrates a method for modelling two flaws into a corresponding penetration flaw in the method for evaluating ductile fracture. The flaws 11 and 12 illustrated in FIG. 2(a), which have the flaw depths $a_1$ 15 and $a_2$ 16, the flaw angles $\theta_1$ 17 and $\theta_2$ 18, and the angle $\alpha$ 19 between the flaws, are modelled into rectangular flaws 21 and 22 illustrated in FIG. 2 (b). That is, the rectangular flaws 21 and 22 have areas expanded in a circumferential direction and in a diameter direction so as to cover the respective flaws 11 and 12. Then, as illustrated in FIG. 2(c), the flaws 21 and 22 are modelled into two penetration flaws 23 symmetrical about an axis 4 by using the following formulae.

$$\theta_{eq} = (a_1\theta_1 + a_2\theta_2)/2t \quad \text{Formula (1)}$$

$$\alpha_{eq} = \alpha + (\theta_2 + \theta_2)/2 - \theta_{eq} \quad \text{Formula (2)}$$

Herein, $\theta_{eq}$ denotes an angle $\theta_{eq}$ 24 corresponding to a flaw length of each penetration flaw 23, and $\alpha_{eq}$ denotes an angle $\alpha_{eq}$ 25 between the penetration flaws 23. In FIG. 2(d), the flaw 21 having the largest area between the flaws 21 and 22 is modelled as a single flaw.

Figure 3A:
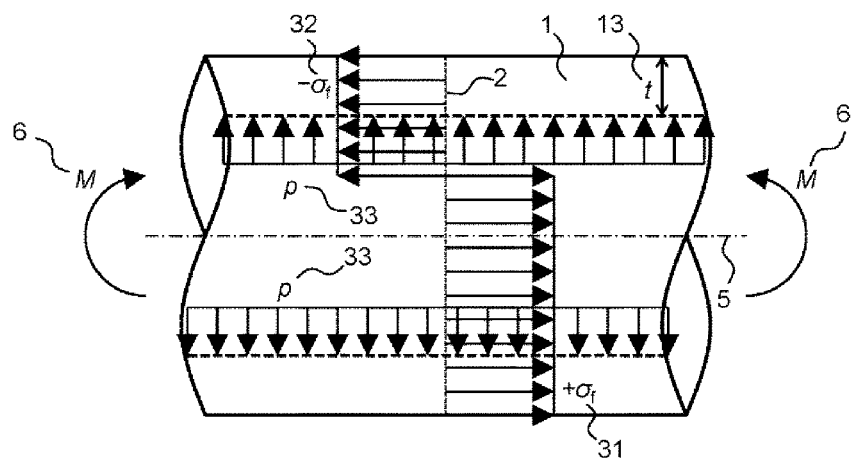
FIGS. 3A and 3B illustrate a stress state in which ductile fracture occurs in a cylinder having flaws due to a bending load.
Figure 3B:
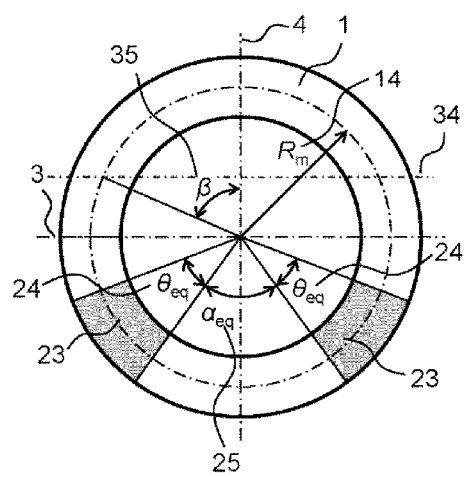

FIG. 3 illustrates a stress state in which ductile fracture occurs in a cylinder having flaws due to a bending load. In the case where the cylinder 1 is made of a ductile material or is used in an environment in which the cylinder has satisfactory toughness, a damage mode assumed when the cylinder 1 receives an excessive load is assumed to be plastic collapse caused by ductile fracture. In evaluation of engineering plastic collapse, distributions of a tensile stress 31 and a compressive stress 32 on the cross-section 2, which are obtained when the bending moment 6 is applied and plastic collapse occurs in the cylinder 1, are indicated by a flow stress $\sigma_f$ as illustrated in FIG. 3(a). Herein, the flow stress $\sigma_f$ is generally defined by an average value of a yield stress $\sigma_y$ and a tensile strength $\sigma_u$ of a material. Herein, the bending moment 6 is applied while an axis 3 vertical to the axis 4 about which the two flaws 23 are symmetrical serves as a rotation axis. At this time, considering the penetration flaws 23 modelled on the cross-section 2, a neutral axis 34 of the tensile stress 31 and the compressive stress 32 in the cross-section 2 does not match with the axis 3. An angle $\beta$ 35 of the neutral axis 34 is calculated on the basis of a balance between the tensile stress 31 and the compressive stress 32 in the cross-section 2. Herein, when an internal pressure p33 is applied to the cylinder 1, the angle $\beta$ 35 of the neutral axis 34 at the time of plastic collapse is indicated by the following formula.

$$\beta = \frac{1}{2}(\pi - \theta_{eq} - \pi p R_m / 2 t \sigma_f) \quad \text{Formula (3)}$$

Herein, $\pi$ denotes a ratio of a circumference of a circle to its diameter, and a unit of an angle is rad. Further, a bending moment $M_C$ 6 at the time of plastic collapse is indicated by the following formula on the basis of a balance with the bending moment 6.

$$M_C = 2\sigma_f R_m^2 t \{2 \sin \beta + \sin \alpha_{eq} - \sin(\alpha_{eq} + \theta_{eq})\} \quad \text{Formula (4)}$$

Herein, when a unit of a stress is MPa and a unit of a length is mm, a unit of a bending moment is Nmm. Further, when the flaw 21 illustrated in FIG. 2 (d) exists in the cross-section 2 of the cylinder 1 as a single flaw, the angle $\beta$ 35 of the neutral axis 34 is similarly indicated by the following formula.

$$\beta = \frac{1}{2}(\pi - \alpha_1 \theta_1 / 2t - \pi p R_m / 2 t \sigma_f) \quad \text{Formula (5)}$$

Furthermore, the bending moment $M_C6$ at the time of plastic collapse with respect to the flaw 21 is indicated by the following formula.

$$M_C = 2\sigma_f R_m^2 t \{2 \sin \beta - (a_1/t)\sin(\theta_1/2)\} \quad \text{Formula (6)}$$

Figure 2A:
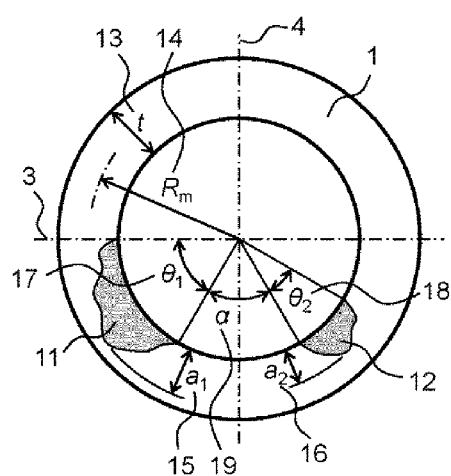
FIGS. 2A-2D illustrate a method for modelling two flaws into a corresponding penetration flaw.
Figure 2B:
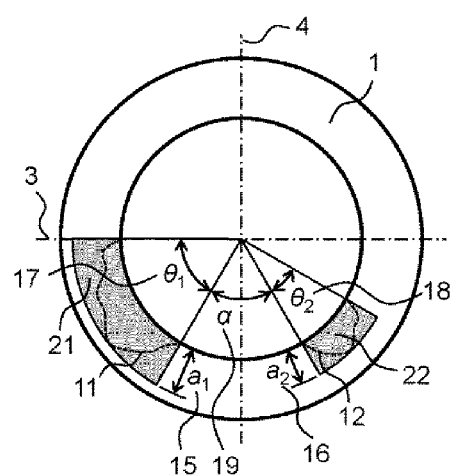
Figure 2C:
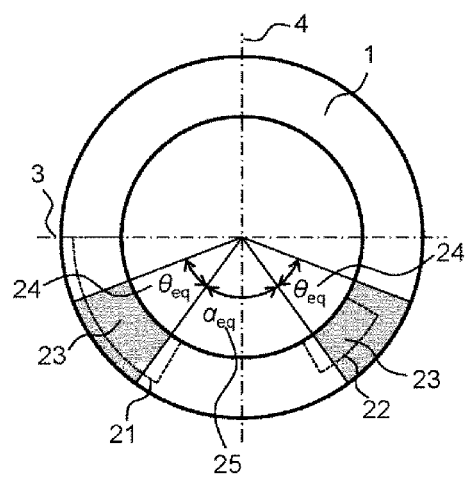
Figure 2D:
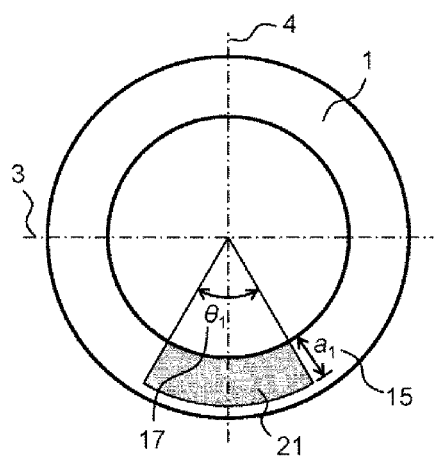

In ductile fracture evaluation of the cylinder 1 having the flaws 11 and 12 illustrated in FIG. 2(a), the bending moment $M_C6$ at the time of plastic collapse, which is calculated by using Formula (3) and Formula (4) with respect to the two symmetrical penetration flaws 23 illustrated in FIG. 2 (c), and the bending moment $M_C6$ at the time of plastic collapse, which is calculated by using Formula (5) and Formula (6) while the flaw 21 having the largest area illustrated in FIG. 2(d) is considered as a single flaw, are compared with each other, and the bending moment $M_C6$ at the time of plastic collapse having a lower value is evaluated as the bending moment $M_C6$ at the time of plastic collapse in FIG. 1(a).

[3. Method for Determining Flaw to be Evaluated in Method for Evaluating Ductile Fracture According to this Embodiment]

FIG. 4 illustrates a method for determining a flaw to be evaluated among a plurality of flaws in the method for evaluating ductile fracture.

Figure 4A:
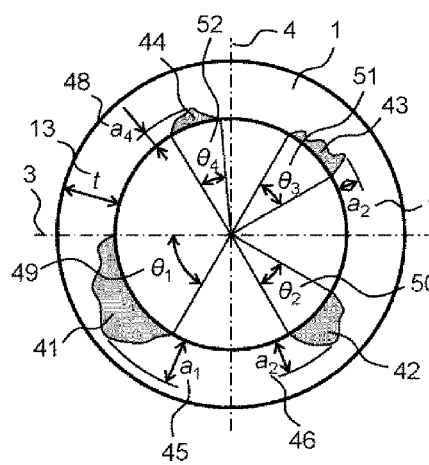
FIGS. 4A-4C illustrate a method for determining a flaw to be evaluated among a plurality of flaws in the method for evaluating ductile fracture.
Figure 4B:
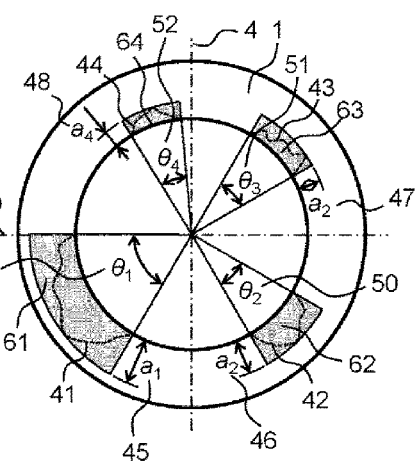
Figure 4C:
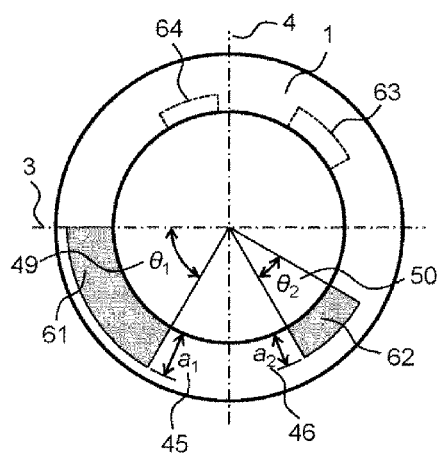

As illustrated in FIG. 4(a), in the case where a plurality of flaws 41, 42, 43, and 44 exist in the cross-section 2 of the cylinder 1, the plurality of flaws 41, 42, 43, and 44 are modelled into respective rectangular flaws 61, 62, 63, and 64 as illustrated in FIG. 4(b) in accordance with [2. Method for evaluating ductile fracture according to this embodiment] described above. Then, as to the axis 3 serving as a rotation axis of the bending moment 6, an angle of the axis 3 at which a total area of the flaws 61, 62, 63, and 64 existing in a region of 180 degrees in which a tensile stress is dominant is the largest is determined as illustrated in FIG. 4(c). Herein, in FIG. 4(c), the angle of the axis 3 at which the total area of the flaws 61, 62, 63, and 64 is the largest exists, but such a difference in angle is not problematic because an influence on the method for evaluating ductile fracture according to this embodiment can be ignored. At this time, only the flaws 61 and 62 existing in the region of 180 degrees in which the tensile stress is dominant with respect to the axis 3 are considered in the method for evaluating ductile fracture. The bending moment $M_C6$ at the time of plastic collapse is evaluated with respect to the flaws 61 and 62 in accordance with [2. Method for evaluating ductile fracture according to this embodiment] described above.

Figure 5A:
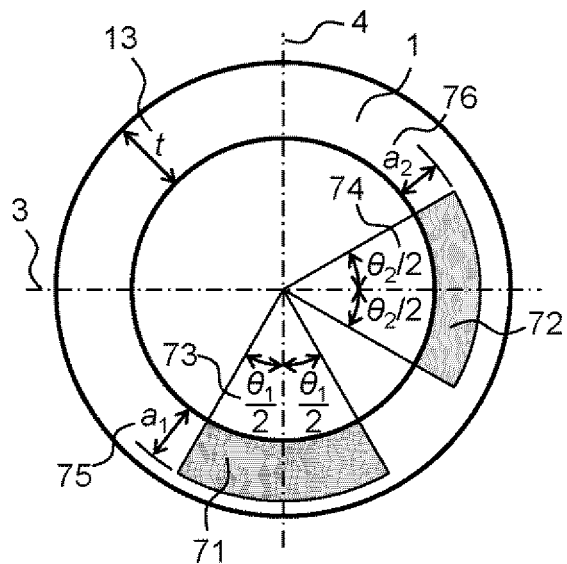
FIGS. 5A and 5B illustrate an example for showing validity of considering only flaws existing in a region of 180 degrees in which a tensile stress is dominant.

FIG. 5 illustrates an example for showing validity of considering only flaws existing in a region of 180 degrees in which a tensile stress is dominant. The bending moment 6 is applied to the pipe 1 while the axis 3 serves as a rotation axis, and a tensile stress is dominant in a region in which a flaw 71 exists. At this time, when flaws 71 and 72 are crack-like flaws, the flaws 71 and 72 are closed in a region of a compressive stress and therefore do not influence on the bending moment $M_C6$ at the time of plastic collapse. Thus, a flaw existing in the region of the compressive stress can be ignored in the ductile fracture evaluation. However, the neutral axis 34 does not match with the axis 3 due to existence of a flaw as illustrated in the stress state at the time of plastic collapse in FIG. 3. Therefore, in order to check whether a part of the flaw 72 or the whole flaw 72 existing on the axis 3 exists in a region of a tensile stress, it is generally necessary to solve a balance formula of a stress in the cross-section 2 while changing the angle β35 of the neutral axis 34 by angles of, for example, 0.1 degree. Herein, the bending moment $M_C6$ at the time of plastic collapse in FIG. 5(a), which is obtained when the angle β35 of the neutral axis 34 is strictly calculated, and the bending moment $M_C6$ at the time of plastic collapse in FIG. 5 (b), which is obtained while the flaw 71 and a part of the flaw 72 existing in the region of 180 degrees in which the tensile stress is dominant with respect to the axis 3 are considered, are calculated.

FIG. 6 is a table showing evaluation conditions of the example of the cylinder having the flaws in FIG. 5. It is considered that an influence of considering flaws existing in the region of 180 degrees in which the tensile stress is dominant with respect to the axis 3 is changed depending on dimensions of the flaws 71 and 72, and therefore evaluation conditions in which flaw angles of the flaws 71 and 72 are changed from 20 degrees to 60 degrees are assumed. Further, flaw depths 75 and 76 of the flaws 71 and 72 are 75% of a thickness t of the cylinder 1.

Figure 5B:
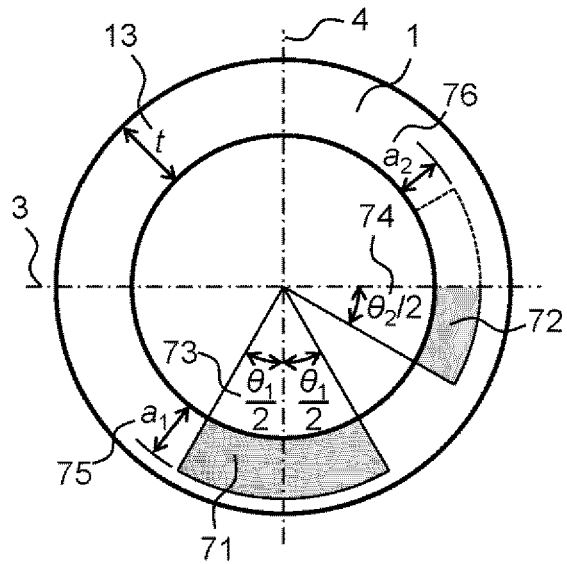

FIG. 7 is a graph showing evaluation results of the example of the cylinder having the flaws in FIG. 5. Results 87 of evaluation A correspond to FIG. 5(a), and results 88 of evaluation B correspond to FIG. 5(b). Each evaluation number 81 corresponds to the evaluation condition shown in the table of FIG. 6, and the calculated bending moment $M_C6$ at the time of plastic collapse is normalized with respect to the result 87 of the evaluation A in each evaluation condition. That is, all the results 87 of the evaluation A are 1.00. Meanwhile, the results 88 of the evaluation B are 1.00 to 1.01. That is, it is found that a difference between the case where the angle β35 of the neutral axis 34 is strictly calculated and the case where only flaws existing in the region of 180 degrees in which the tensile stress is dominant are considered is about 1% and can therefore be ignored in terms of engineering.

Therefore, in the case where the plurality of flaws 41, 42, 43, and 44 exist in the cross-section 2 of the cylinder 1 illustrated in FIG. 4, the angle of the rotation axis 3 of the bending moment 6 at which the total area of the flaws 61, 62, 63, and 64 existing in the region of 180 degrees in which the tensile stress is dominant is the largest is determined as illustrated in FIG. 4(c), and only the flaws 61 and 62 existing in the region of 180 degrees in which the tensile stress is dominant with respect to the axis 3 are considered in the method for evaluating ductile fracture.

[4. Method for Determining Corresponding Penetration Flaw in Method for Evaluating Ductile Fracture According to this Embodiment]

FIG. 8 illustrates a method for modelling a plurality of flaws into two symmetrical flaws. FIG. 9 illustrates a method for modelling a plurality of flaws into three symmetrical flaws.

Figure 8A:
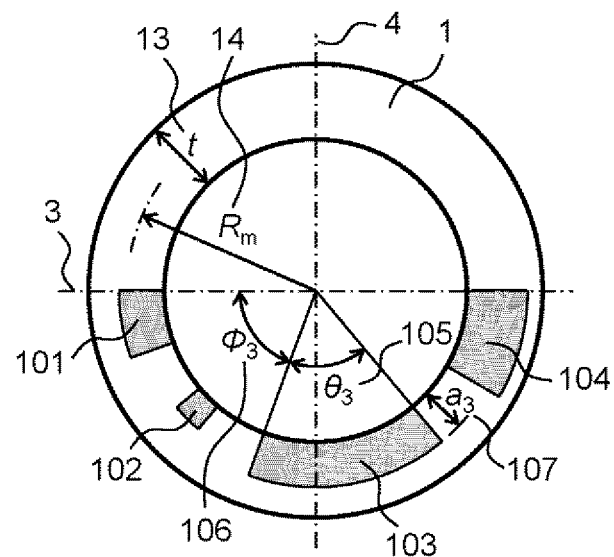
FIGS. 8A and 8B illustrate a method for modelling a plurality of flaws into two symmetrical flaws.
Figure 8B:
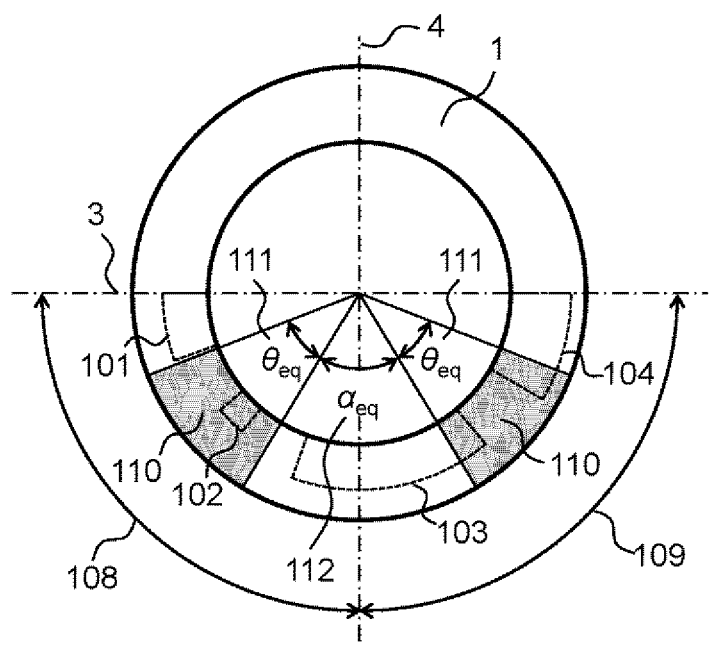
Figure 9A:
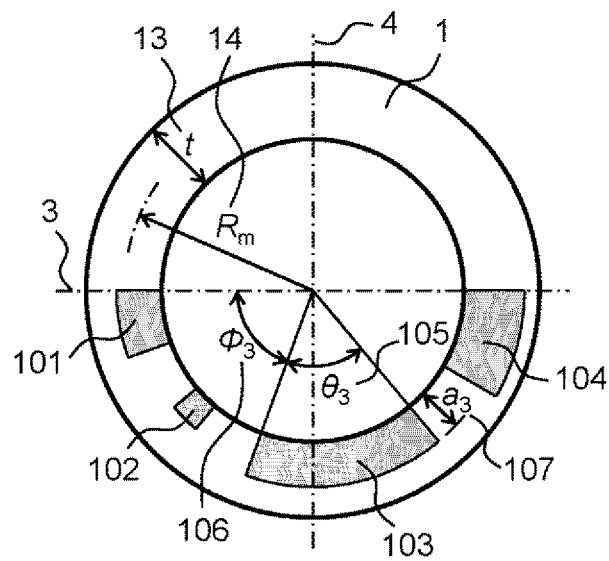
FIGS. 9A and 9B illustrate a method for modelling a plurality of flaws into three symmetrical flaws.
Figure 9B:
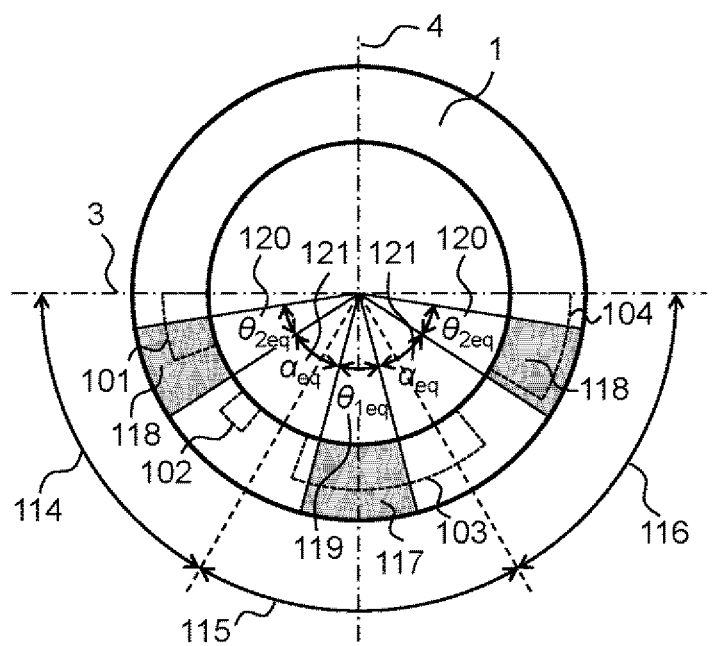

As illustrated in FIG. 8(a), a plurality of flaws 101, 102, 103, and 104 exist in a region in which a tensile stress is dominant with respect to the rotation axis 3 in the cross-section 2 of the cylinder 1. At this time, for example, a position of the flaw 103 is defined by an angle $\varphi_3$ 106 from the rotation axis 3. Similarly, positions of the flaws 101, 102, and 104 are also defined by an angle φ from the rotation axis 3. Note that the angle φ is not necessarily an angle from the rotation axis 3. In order to model the flaws 101, 102, 103, and 104 into two corresponding penetration flaws 110 or three corresponding penetration flaws 117 and 118, the region of 180 degrees is divided into two ranges 108 and 109 each of which has 90 degrees in FIG. 8(b) or three ranges 114, 115, and 116 each of which has 60 degrees. For example, the angle $\theta_{eq}$ corresponding to a flaw length of a corresponding penetration flaw in the range 108 of 90 degrees in FIG. 8(b) is calculated by the following formula.

$$\theta_{eq} = \text{Sum}(a_k \theta_k/t) \quad \text{Formula (7)}$$

Herein, in the case where n flaws exist in the range 108 of 90 degrees, Sum $(a_k\theta_k)$ indicates a sum total of $a_1\theta_1$ to $a_n\theta_n$. Note that $\theta_k$ is a flaw angle $\theta$ existing in the range 108. That is, in the case where a half of a flaw having 0 of 60 degrees, i.e., 30 degrees exist in the range 108, $\theta$ is 30 degrees in Formula (7). Further, an angle $\varphi_{eq}$ indicating a position of a flaw is calculated by the following formula.

$$\varphi_{eq} = \text{Sum}\{(\varphi_k + \theta_k/2)a_k\theta_k\}/\text{sum}(a_k\theta_k) \quad \text{Formula (8)}$$

Herein, as to the flaw angle $\theta_{eq}$ and the angle $\varphi_{eq}$ calculated by using Formula (7) and Formula (8), the penetration flaw in the range 108 is set to be $\theta_{1eq}$ and $\varphi_{eq}$, and the penetration flaw in the range 109 is set to be $\theta_{2eq}$ and $\varphi_{eg}$. At this time, in order to model the penetration flaws calculated in the ranges 108 and 109 each of which has 90 degrees into the two penetration flaws 110 symmetrical about the axis 4, a flaw angle $\theta_{eq}$ 111 and an angle $\alpha_{eq}$ 112 between the flaws are calculated by the following formula.

$$\theta_{eq} = (\theta_{1eq} + \theta_{2eq})/2 \quad \text{Formula (9)}$$

$$\alpha_{eq} = (\varphi_{2eq} - \theta_{1eq}) \quad \text{Formula (10)}$$

The bending moment $M_C6$ at the time of plastic collapse is evaluated with respect to the two penetration flaws 110 symmetrical about the axis 4 modelled by using Formula (7) to Formula (10) in accordance with [2. Method for evaluating ductile fracture according to this embodiment] described above.

As illustrated in FIG. 9(*b*), in the case where the region is divided into the three ranges 114, 115, and 116 each of which has 60 degrees, the flaw angle $\theta_{eq}$ and the angle $\varphi_{eq}$ in each of the ranges 114, 115, and 116 are calculated by using Formula (7) and Formula (8). Further, the penetration flaw 117 in the range 115 has the flaw angle $\theta_{1eq}$ and is placed so that the axis 4 is the center. The flaw in the range 114 and the flaw in the range 116 are modelled into the two penetration flaws 118 symmetrical about the axis 4 by using Formula (9) and Formula (10). Herein, when an angle between the penetration flaws 118 in the ranges 114 and 116, which is calculated by using Formula (10), is $\alpha''_{eq}$, an angle $\alpha_{eq}$ 121 between the flaws in FIG. 9(*b*) is calculated by the following formula.

$$\alpha_{eq} = (\alpha'_{eq} - \theta_{1eq})/2 \quad \text{Formula (11)}$$

As illustrated in FIG. 9(*b*), as to the modelled three penetration flaws 117 and 118 symmetrical about the axis 4, the angle $\beta$35 of the neutral axis 34 at the time of plastic collapse is calculated by the following formula, and the bending moment $M_C6$ is calculated by the following formula.

$$\beta = \tfrac{1}{2}(\pi - \theta_{1eq}/2 - \theta_{2eq} - \pi p R_m/2t\sigma_f) \quad \text{Formula (12)}$$

$$M_C = 2\sigma_f R^2 t \{2 \sin \beta + \sin(\theta_{1eq}/2 + \alpha_{eq}) - \sin(\theta_{1eq}/2) - \sin(\theta_{1eq}/2 + \alpha_{eq} + \theta_{2eq})\} \quad \text{Formula (13)}$$

In order to model the flaws into the three penetration flaws 117 and 118 symmetrical about the axis 4, the bending moment $M_C6$ at the time of collapse, which is calculated by using Formula (12) and Formula (13), and the bending moment $M_C6$ at the time of plastic collapse, which is calculated by using Formula (5) and Formula (6) while a flaw having the largest area is considered as a single flaw, are compared with each other, and a lower value is evaluated as the bending moment $M_C6$ at the time of plastic collapse.

Similarly, the bending moment $M_C6$ at the time of plastic collapse can also be evaluated by dividing the region of 180 degrees in which the tensile stress is dominant with respect to the rotation axis 3 in the cross-section 2 of the cylinder 1 into four or more parts.

In order to verify validity of this modelling method, the bending moment $M_C6$ at the time of plastic collapse was evaluated assuming that four flaws exist. The four flaws are a flaw having a flaw depth ratio $a_1/t$ of 0.6 and a flaw angle $\theta_1$ of 20 degrees in a position at an angle $\varphi_1$ of 0 degree, a flaw having $a_2/t$ of 0.4 and $\theta_2$ of 10 degrees in a position at $\varphi_2$ of 40 degrees, a flaw having $a_3/t$ of 0.6 and $\theta_3$ of 60 degrees in a position at $\varphi_3$ of 70 degrees, and a flaw having $a_4/t$ of 0.8 and $\theta_4$ of 30 degrees in a position at $\varphi_4$ of 150 degrees. That is, because the flaws exist in the range of 180 degrees, all the flaws are considered in the ductile fracture evaluation. When the bending moment $M_C6$ at the time of plastic collapse obtained by modelling of flaws into two penetration flaws in FIG. 8 and modelling of flaws into three penetration flaws in FIG. 9 was divided by the bending moment $M_C6$ at the time of plastic collapse directly calculated with respect to shapes of the assumed flaws, a result thereof was 1.00 in each modelling. Therefore, in this example, an influence of modelling on the bending moment $M_C6$ at the time of plastic collapse is 1% or less, and validity of the method for evaluating ductile fracture according to this embodiment was verified.

[5. Method and Apparatus for Evaluating Ductile Fracture According to this Embodiment]

An apparatus that can implement the method for evaluating ductile fracture according to this embodiment will be described. In the case where a cylindrical structure in which a plurality of flaws exist receives a bending load, the apparatus according to this embodiment calculates a collapse load assuming that ductile cracks are developed from the flaws and collapse occurs. Herein, it is possible to calculate a bending moment, a bending stress, and the like at the time of collapse on the basis of the collapse load.

FIG. 10 shows an apparatus that can implement the method for evaluating ductile fracture according to this embodiment. As shown in FIG. 10, the apparatus includes an input device 200, a storage device 210, a collapse load calculation device 220, a collapse load determination device 230, and an output device 240. The input device is a keyboard, a mouse, or the like, and a cylindrical shape 201, a load condition 202, a flaw shape 203, and a material physical property 204 are input therethrough. Herein, the material physical property 204 can also be selected from a material physical property database 211 stored in a storage device constituted by a RAM (Random Access Memory), a ROM (Read Only Memory), an HDD (Hard Disk Drive), or the like. Input of the cylindrical shape 201, the load condition 202, the flaw shape 203, and the material physical property 204 to the input device 200 is stored in an input data unit 212 of the storage device 210. Information is loaded from the input data of the input data unit 212 in the storage device to the collapse load calculation device 220 including a RAM (Random Access Memory), a CPU (Central Processing Unit), and the like. In a single flaw selection unit 221, a flaw having the largest area among a plurality of flaws is considered as a single flaw, and a collapse load calculation unit 222 calculates a collapse load with respect to the single flaw in accordance with the method described in [2. Method for evaluating ductile fracture according to this embodiment] mentioned above. A plurality of flaws modelling unit 223 models the flaws into symmetrical penetration flaws in which areas of the flaws are the same and center axes match with each other, and a collapse load calculation unit 224 calculates a collapse load of the modelled flaws in accordance with the methods described in [2. Method for evaluating ductile fracture according to this embodiment] to [4. Method for determining corresponding penetration flaw in method for evaluating ductile fracture according to this embodiment] described above. Results of the collapse load calculation units 222 and 224 are stored in a collapse load calculation result unit 213, and the minimum collapse load is determined by the collapse load determination device 230. A result thereof is displayed by the output device 240 including a display.

FIG. 11 shows a processing flow of the method for evaluating ductile fracture according to this embodiment. In S000, ductile fracture evaluation is started. In S0001 to S0004, a cylindrical shape (outer diameter $D_0$, thickness t), a load condition (internal pressure p), a flaw shape (flaw depths $a_1$, $a_2$, flaw angles $\theta_1$, $\theta_2$, angle $\alpha$ between flaws), and physical properties of a material (yield stress $\sigma_y$, tensile strength $\sigma_u$, flow stress $\sigma_f$) are set. In S005, flaws are modelled into rectangular flaws. In S006, a flaw to be evaluated is determined in accordance with [4. Method for determining corresponding penetration flaw in method for evaluating ductile fracture according to this embodiment]. In S007 to S008, a flaw having the largest area among the plurality of flaws is considered as a single flaw, and a collapse load is calculated in accordance with the above method. In S009 to S010, the flaw having the largest area among the plurality of flaws is considered as a single flaw, and the flaws are modelled into symmetrical penetration flaws in which areas of the flaws are the same and center axes match with each other, and then a collapse load is calculated in accordance with the methods in [2. Method for evaluating ductile fracture according to this embodiment] to [4. Method for determining corresponding penetration flaw in method for evaluating ductile fracture according to this embodiment] described above. In S011, the minimum collapse load is determined, and a result thereof is displayed in S012.

In the above description, according to the invention, in the case where a plurality of flaws are generated in a cylindrical structure that receives a bending load, it is possible to provide a simple method and device for evaluating a collapse load of a structure with respect to ductile fracture.

Note that, in the case where a bending load is applied to a flaw and the flaw receives a tensile stress, fracture occurs with a low load, and, in the case where the cylinder is rotated in the circumferential direction at 180 degrees and the flaw is located in a compressive stress region, fracture occurs with a higher load. Although a single flaw can be simply evaluated, a plurality of flaws interact with each other, and therefore it is difficult to specify a load direction that causes fracture with the lowest load. Thus, in the invention, a load applied in a certain direction is calculated with respect to a plurality of penetration flaws, but such a fracture load applied in the certain direction and the actual smallest fracture load are different depending on a condition in some cases. In this case, the actual smallest fracture load is close to a fracture load evaluated with respect to a single flaw, and therefore a collapse load, which is evaluated while a flaw having the largest area among the plurality of flaws is considered as a single flaw, and a collapse load, which is calculated by modelling the plurality of flaws into corresponding symmetrical penetration flaws, are calculated and compared with each other. With this, it is possible to simply evaluate a collapse load of a structure.

Further, the invention is not limited to the above examples and includes various modification examples. For example, the above examples have been described in detail to easily understand the invention, and therefore the invention is not necessarily limited to the examples having all the configurations described above. Further, a part of a configuration of a certain example can be replaced with a configuration of another example, and a configuration of another example can be added to a configuration of a certain example. Further, another configuration can be added to, removed from, or replaced with a part of the configuration of each example.

REFERENCE SIGNS LIST

1: cylinder
2: flaw cross-section vertical to axis direction
6: bending moment
11, 12: flaw
23: modelled penetration flaw

The invention claimed is:
1. An apparatus for evaluating ductile fracture in the case where a cylindrical structure in which a plurality of circumferential flaws exist receives a bending load, comprising:
   a collapse load calculation unit for selecting a flaw having the largest area from the plurality of flaws to calculate a collapse load and modelling the plurality of flaws into a plurality of penetration flaws to calculate a collapse load; and
   a collapse load determination unit for selecting a smallest value of the calculated collapse loads.

* * * * *